United States Patent [19]

Hartstein

[11] 4,262,370
[45] Apr. 21, 1981

[54] SUTURELESS INTRAOCULAR LENS

[75] Inventor: Jack Hartstein, Creve Coeur, Mo.

[73] Assignee: Bausch & Lomb Incorporated, Rochester, N.Y.

[21] Appl. No.: 711,540

[22] Filed: Aug. 4, 1976

[51] Int. Cl.³ .................... A61F 1/16; A61F 1/24
[52] U.S. Cl. ........................................................ 3/13
[58] Field of Search ........................................ 3/13, 1

[56] References Cited

U.S. PATENT DOCUMENTS

| 2,834,023 | 5/1958 | Lieb | 3/13 X |
| 3,922,728 | 12/1975 | Krasnov | 3/13 |
| 4,056,855 | 11/1977 | Kelman | 3/13 |
| 4,085,467 | 4/1978 | Rainin et al. | 3/13 |

FOREIGN PATENT DOCUMENTS

| 959314 | 3/1957 | Fed. Rep. of Germany | 3/13 |
| 1103399 | 5/1955 | France | 3/13 |

Primary Examiner—Ronald L. Frinks
Attorney, Agent, or Firm—Gravely, Lieder & Woodruff

[57] ABSTRACT

An intraocular lens which can be inserted and fixed in the eye by means of retaining members which are positioned in openings in the iris in an essentially sutureless technique. The lens does not move with the pupil during dilation and contraction and resists becoming dislodged or dislocated in the eye.

3 Claims, 11 Drawing Figures

SUTURELESS INTRAOCULAR LENS

REFERENCE TO PRIOR APPLICATIONS

In my previously filed copending application Ser. No. 526,509 filed Nov. 25, 1974 entitled "INTRAOCULAR LENS," (now abandoned), I have disclosed a lens suitable for placement in the eye following entracapsular extraction. In copending application Ser. No. 547,620 filed Feb. 6, 1975, entitled "INTRAOCULAR LENS FOR INTRACAPSULAR EXTRACTION," (now abandoned), I have disclosed a lens suitable for insertion in the eye following extracapsular extraction. In copending application of Hartstein and Platt Ser. No. 638,610 filed Dec. 8, 1975, entitled "BIFOCAL INTRAOCULAR LENS" (now abandoned) is shown a number of intraocular lens with bifocal portions therein.

BACKGROUND OF THE INVENTION

This invention relates to the art of medicine and has particular reference to artificial lenses employed in ophthalmology for correction of aphakia and restoration of binocular vision.

In the late 1940's Ridley inserted the first intraocular lens into the posterior chamber of the eye. Subsequently, the work of Epstein and Binkhorst was directed toward a lens positioned in the anterior chamber and supported by the iris. The so-called "Iris Clip Lens" has legs aligned on the top and bottom of the iris about 180° from each other and is designed to clip onto the iris. Fedorov U.S. Pat. No. 3,673,616 shows a modification of the iris clip lens involving three posterior loops and three antenna-like extensions in front of the iris. Binkhorst also has developed a lens designed for anchoring to the cleft between the iris and the capsular membrane by iridocapsular adhesions following the extracapsular extraction. Worst had developed a lens having an anchor on the iris at right angles to the posterior legs, which lens is used primarily following intracapsular extraction, although it can be used following extracapsular extraction.

In my copending applications Ser. Nos. 526,509; 547,620; and 638,610, of which I am solo or joint inventor, the intraocular lens shown in said applications all require suturing to the iris by means of a flange with openings therethrough which allows the lens to be sutured to the iris. Similarly Otter U.S. Pat. No. 3,906,551 shows a lens which has a haptic rim with suture openings therein for fixation to the iris. It would be desirable if the lens could be fastened to the iris without suturing as this would allow a simpler implantation and would obviate the possibility that the suture would become dislodged or break loose after implantation.

Other forms of the Otter disclosure show lens anchored by means of clips rather than sutures, but these devices are loosely positioned in the iridectomy and are not stable in the eye in the vertical or horizontal directions.

The invention of application Ser. No. 526,509 is specifically designed to be used after clean extracapsular extraction. In this type procedure the posterior chamber and the capsular membrane are thoroughly cleaned of all cortial material by an aspirator or like device.

The invention of application Ser. No. 547,620 is specifically designed to be used after intracapsular extraction. In this type procedure the entire cataract and the capsular membrane are removed so that the intraocular lens which is implanted must be anchored to the iris.

The invention of application Ser. No. 638,610 is directed to a bifocal intraocular lens which allows the patient both distance and near vision without the wearing of eyeglasses.

In all of these applications the lens is sutured to the superior portion of the iris, and the sphincter muscle, which controls dilation of the pupil, is avoided to make the position of the lens independent of the pupil size.

It is, therefore, the principal object of the present invention to provide an intraocular lens which is inserted and fixedly positioned with respect to the iris of the eye without the necessity for suturing the same. It is a further object of the present invention to provide an intraocular lens which can be used with either extracapsular or intracapsular extraction and which can be inserted into the eye by use of anchor means which are inserted into incisions in the iris and fixed thereto without the use of sutures.

Still another object of the present invention is to provide a sutureless technique for inserting artificial lens into the eye such that the lens will not move with the eye during dilation and contraction of the pupil and will resist being dislodged from a prefixed position in the eye.

These and other objects and advantages will become apparent hereinafter.

SUMMARY OF THE INVENTION

The present invention comprises an intraocular lens for insertion into the eye either following extracapsular or intracapsular extraction, said lens having means for anchoring the same to the iris of the eye without sutures so that the lens will not move when the pupil dilates and contracts and will resist being dislodged from its fixed position in the eye.

DETAILED DESCRIPTION

Figure 2:
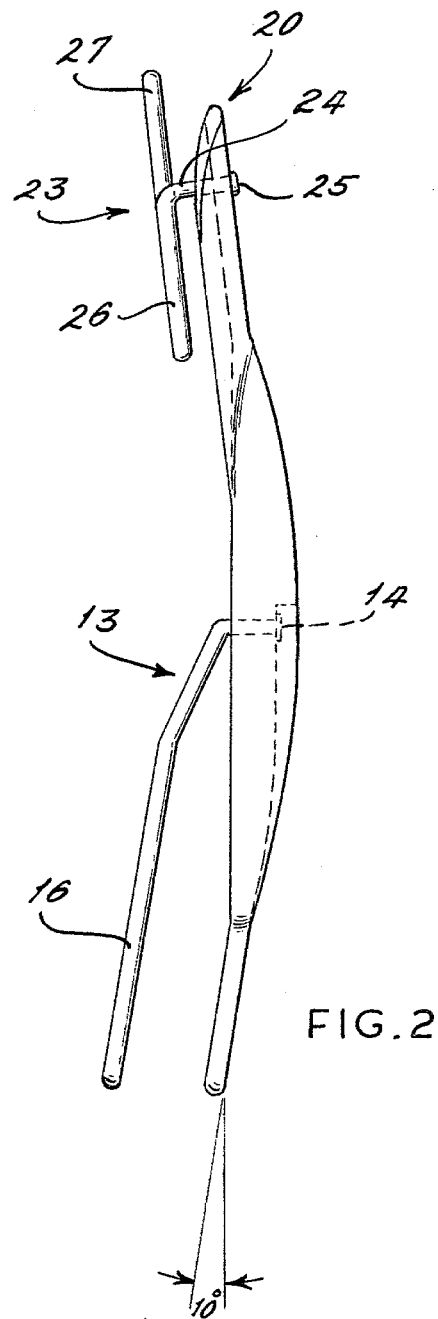
FIG. 2 is a side elevational view of the lens shown in FIG. 1.
Figure 1:
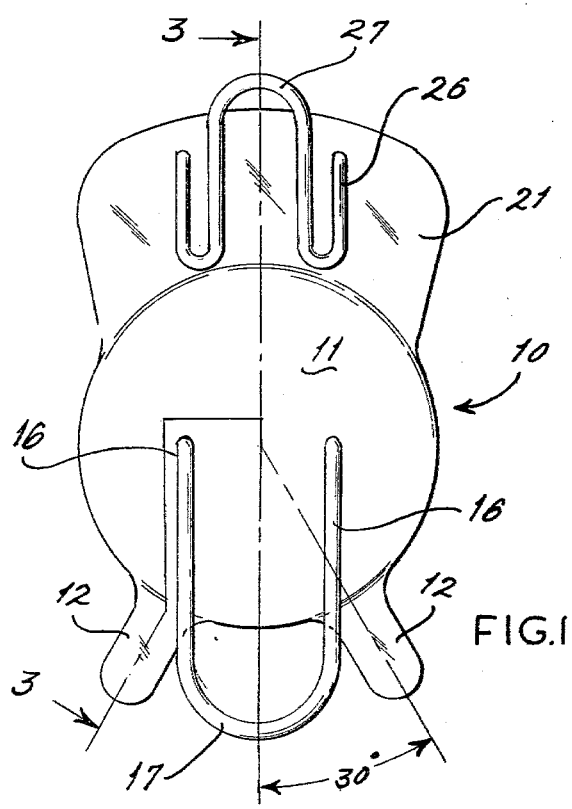
FIG. 1 is a back elevational view of one embodiment of the invention.

FIG. 1 shows a lens 10 having a central lens portion 11 with inferior anterior anchor means 12 integral therewith. The anchor means 12 comprises diverging tabs positioned about 30° from the vertical centerline "A" of the lens 10. The tabs 12 extend rearwardly at an angle of about 10° from the central portion 11 (FIG. 2).

A posterior anchor 13 is secured to the central portion 11 by means of a head 14 positioned in the front face of the central portion 11. The posterior anchor 13 comprises leg portions 16 which are connected at their ends by a bight member 17. The leg portions 16 extend at substantially the same angle with respect to the central portion 11 as to the anterior tabs 12. The inferior portion of the iris 18 is gripped between the anterior anchor means 12 and the posterior anchor means 13 (FIG. 3) so that the sphincter muscle at the internal periphery of the iris is free to move with respect to the lens 10.

The unique superior anchor of this invention is designated by the numeral "20" and comprises the anterior anchor flange 21 which extends outwardly about 2 mm from the lens central portion 11. The flange 21 is slightly convex as shown in FIG. 2 to conform to the curvature of the superior portion 22 of the iris. Secured adjacent to the outer periphery of the flange 21 is a sutureless anchor means 23 which comprises a rearwardly extending anchor leg 24 secured in the flange 21 by a head 25, and a continuous anchor loop which is spaced about 0.6 mm from the rear surface of the flange 21 and has feet portions 26 and 27 extending toward and away from the central portion 11 respectively. The portions 26 and 27 are positioned between the anchor posts 24 and extend away from said posts 24 toward the periphery of the flange 21 and toward the central lens portion 11. Stated another way, the loop feet portions 26 and 27 extend at substantially right angles to a line connecting the posts 24 and extend on both sides of said line. The portions 26 and 27 are designed to be slipped into an incision cut in the superior portion of the iris 22 behind the sphincter muscle. Thus the lens is independent of contraction and dilation of the pupil which is controlled by the sphincter muscle.

The lens 11, the anterior tabs 12 and the flange 21 are all molded in one piece from a plastic such as polymethyl methacrylate. The anchors 13 and 23 are a platinum wire of about 0.15 mm to about 0.2 mm in diameter.

The lens 10 is anchored into the eye merely by the surgeon making a lateral incision in the superior portion of the iris, slipping the anchor 23 in through the incision to position the lens 10 in the iris and then slipping the inferior portion of the iris 18 between the anchors 12 and 16.

The flange 21 extends away from the lens body 11 at an angle of about 10° from the central portion 11 and the loop portions 27 and 27 are substantially parallel to the flange 21 and at the same angle with respect to the central portion 11.

Figure 3:
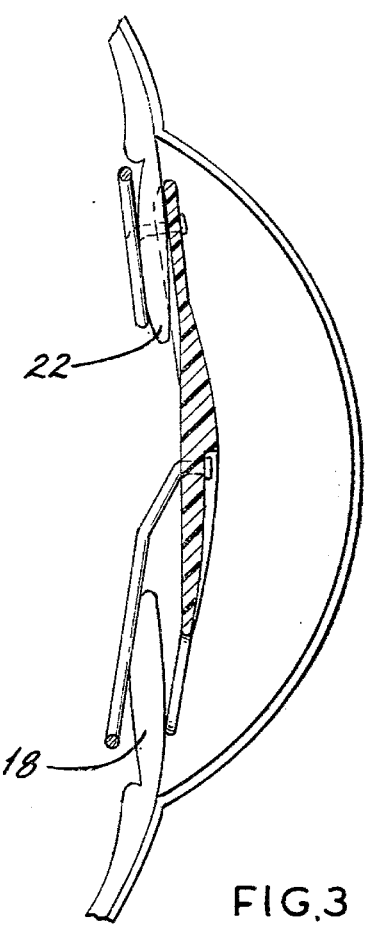
FIG. 3 is a sectional view taken along lines 3—3 of FIG. 1 with the lens positioned in the eye which is represented diagrammatically.
Figure 4:
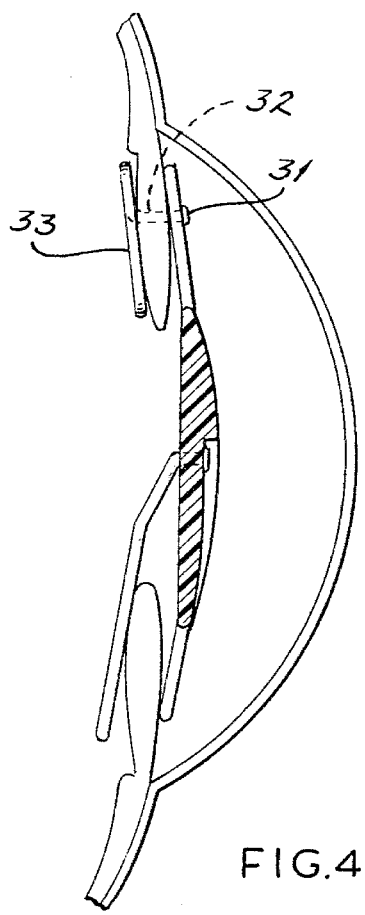
FIG. 4 is a side elevational view partly in section and partly diagrammatic of a modification of the invention presently in the eye.
Figure 5:
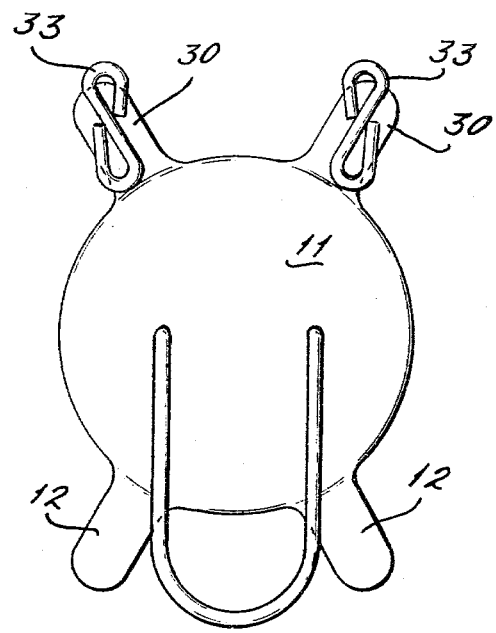
FIG. 5 is a back view of the lens of FIG. 4.

FIGS. 4 and 5 show a modification of the present invention in which the superior anterior and posterior anchors are changed from that shown in FIGS. 1-3.

In FIGS. 4 and 5, the superior anchor means is a pair of opposed anterior tabs 30 positioned at about 30° from the vertical centerline of the central lens portion 11. The tabs 30 are aligned with and opposed to the inferior anterior tabs 12. Extending rearwardly from the outer ends of the tabs 30 are superior posterior anchor means which comprise a rearwardly extending leg 32 retained in the tab 30 by a head 31 and connecting to a figure "8" shaped posterior foot portion 33. Each of the "8" shaped members 33 is designed to be inserted through an incision in the iris behind the sphincter muscle and to retain the lens in the eye independently of dilation and contraction of the pupil. The "8" shaped foot is at the same 10° angle with respect to the lens center 11 as are the anterior tabs 30. The tabs 12 and 30 are molded integrally with the lens body 11 of polymethyl methacrylate plastic. The anchors 31-33 are of platinum wire and are one piece with the foot 33 being formed into substantially the "8" shape by being bent on itself.

Figure 6:
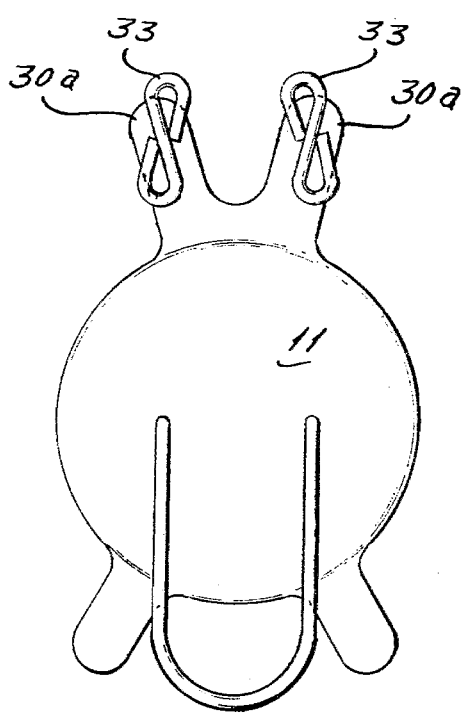
FIG. 6 is a back view of a further modification of the invention.

FIG. 6 shows a slight modification of the structure of FIGS. 4 and 5 in which the superior anterior tabs 30a are slightly longer than the tabs 30 of FIGS. 4 and 5 and the tabs 30a are positioned at about a 15° angle with respect to the vertical centerline of the lens 11.

Figure 7:
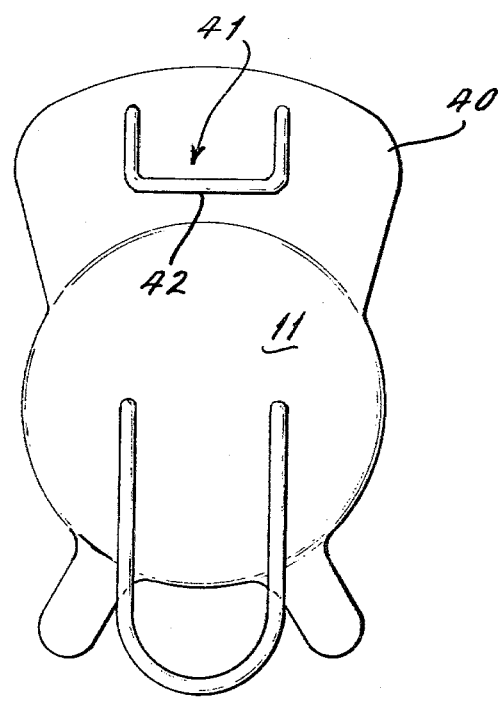
FIG. 7 is a back view of another modification of the invention.
Figure 8:
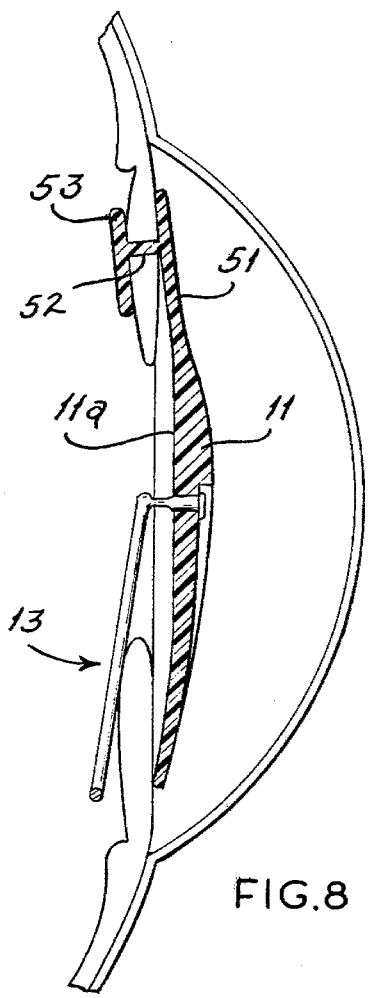
FIG. 8 is a side elevational view partly in section and partly diagrammatic of another modification of the invention showing the lens in place in the eye.
Figure 10:
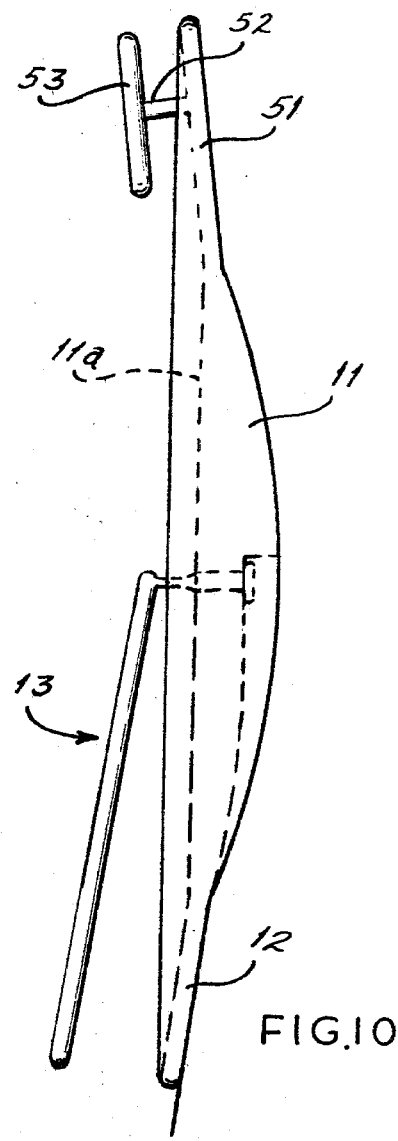
FIG. 10 is an enlarged detailed side elevational view of the lens shown in FIG. 8.
Figure 9:
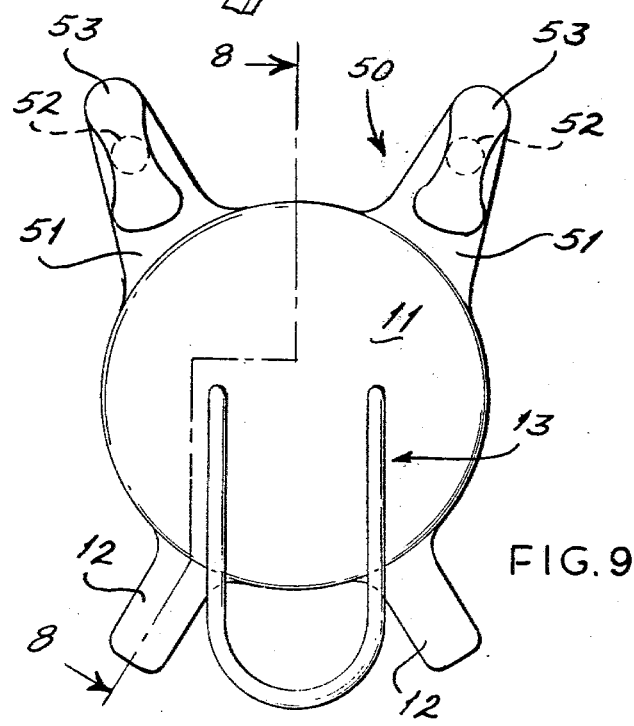
FIG. 9 is a back view of the lens shown in FIG. 8.
Figure 11:
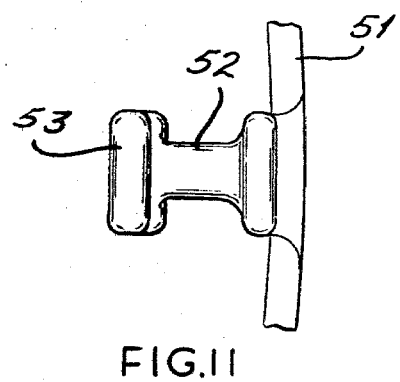
FIG. 11 is an enlarged fragmentary plan view of the lens shown in FIG. 10.

FIG. 7 shows another modification of the invention utilizing a one piece molded anterior superior anchor 40 and a superior posterior anchor 41 in the form of a hook having a depending portion 42 bent inwardly toward the central lens 11 and spaced from the anterior anchor 40 about the thickness of the iris. In this application the hook 42 is inserted through an incision in the iris behind the sphincter muscle.

FIGS. 8-11 show a preferred form of the invention in which the entire lens except for the posterior inferior anchor 13 is molded from one piece of plastic, preferably polymethyl methacrylate. This is therefore a self-fixating and self-retaining lens and does not depend on extraneous wire members for fixation in the eye.

The inner surface 11a of the center lens member 11 is dish shaped and concave to assist in forming and finishing. The superior anchors 50 comprise an anterior portion 51 whose centerline is aligned substantially with the centerline of the opposed anterior inferior leg 12. The anterior legs 51 are at about a 30° angle with respect to the vertical center line of the center lens 11. Connected to the tabs 51 and rearwardly depending therefrom are reduced legs 52 connected to dumbbell shaped anchors 53 which are substantially aligned with the axis of the opposed tabs 51. The dumbbell shaped feet 53 are designed to be slipped through incisions in the iris behind the sphincter muscle and to embrace the iris between the foot 53 and the tabs 51 to retain the lens 11 in the eye securely without sutures.

The feet 53 extend toward and away from the central lens portion 11 and preferably are substantially aligned with the centerline of the anterior tabs 51.

What is claimed is:

1. An intraocular lens for implantation in the eye comprising:
  (a) a central lens portion,
  (b) inferior anchor means fastened to the said lens portion and adapted to position the lens with respect to the inferior portion or the iris while allowing the iris to move with respect to the said lens, and
  (c) superior anterior and posterior anchor means integral with the lens body adapted to engage the superior portion of the iris to fix the lens in a position relative to the said superior portion of the iris while allowing the pupil to expand and contract without the lens moving relative to said iris, said superior anchor means being adapted to be fastened to the iris without the application of sutures or other outside fastening means, said anterior anchor comprising diverging tabs and said posterior anchor comprises means anchored in each tab and extending rearwardly thereof with foot portions at substantially right angles thereto and defining with the tabs a space adapted to retain the iris, the posterior anchor means being adapted to be positioned in the iris behind the sphincter muscle to allow contraction and dilation of the pupil without affecting movement of the lens.

2. The lens of claim 1 wherein the posterior and anterior superior anchors are of one piece construction.

3. The lens of claim 2 wherein the anterior and posterior anchors are connected by a reduced section.

* * * * *